United States Patent [19]

Saito et al.

[11] Patent Number: 5,213,604

[45] Date of Patent: May 25, 1993

[54] PROCESS FOR PREVENTING CHEMICAL INJURIES TO VEGETABLES, FRUITS OR FLOWERS CAUSED BY FUMIGATION AND AGENT FOR ELIMINATING METHYL BROMIDE

[75] Inventors: Hitoshi Saito; Shigeo Hayashimoto; Mutsumi Matsumoto, all of Gunma, Japan

[73] Assignee: Nippon Kayaku Kabushiki Kaisha, Tokyo, Japan

[21] Appl. No.: 793,605

[22] Filed: Nov. 18, 1991

[30] Foreign Application Priority Data

Nov. 29, 1990 [JP] Japan ................. 2-325447

[51] Int. Cl.$^5$ .................. A01N 3/02; A01N 29/02; A23L 3/3526; A23L 3/358
[52] U.S. Cl. .................... 504/114; 426/286; 504/103; 504/111; 504/105; 504/115
[58] Field of Search ............... 71/68, 92, 121; 426/286

[56] References Cited

U.S. PATENT DOCUMENTS 4,917,820  4/1990  Matsumoto et al. ............. 252/397

OTHER PUBLICATIONS

Morrison et al., *Organic Chemistry*, Allyn and Baron: Boston, pp. 174–177, 943–948, 1987.

*Primary Examiner*—Allen J. Robinson
*Assistant Examiner*—S. Mark Clardy
*Attorney, Agent, or Firm*—Nields & Lemack

[57] ABSTRACT

The present invention is concerned with a process for preventing chemical injuries to vegetables, fruits or flowers caused by methyl bromide, which comprises keeping the vegetables, fruits or flowers, which have been fumigated with methyl bromide, together with (A) an agent for eliminating methyl bromide comprising at least one compound selected from the group consisting of chloric acid, chlorous acid, hypochlorous acid, phosphoric acid, phosphorous acid, hypophosphorous acid and salts thereof and/or (B) an amine. According the present invention, the chemical injuries to vegetables, fruits or flowers caused by methyl bromide can be easily prevented.

7 Claims, No Drawings

PROCESS FOR PREVENTING CHEMICAL INJURIES TO VEGETABLES, FRUITS OR FLOWERS CAUSED BY FUMIGATION AND AGENT FOR ELIMINATING METHYL BROMIDE

DETAILED DESCRIPTION OF THE INVENTION

1. Field of Industrial Application

This invention relates to a process for preventing chemical injuries to vegetables, fruits or flowers caused by methyl bromide remaining after fumigating them and an agent for eliminating methyl bromide.

2. Prior Art

Plant quarantine systems have been developed in various countries in order to prevent the invasion of disease and insect pest, which seriously damage crops, into their own countries. When disease or insect pest is found by an inspection of imported plants, these plants are disinfected by, for example, fumigation or discarded. It is sometimes required, according to the types or growing districts of vegetables, fruits or flowers, to preliminarily fumigate the products in the growing areas (countries). Common fumigants include hydrocyanic acid and methyl bromide. In the case of the fumigation with methyl bromide, in particular, chemical injuries to vegetables, fruits or flowers are sometimes observed depending on the types of them or the employed fumigation conditions. Namely, the vegetables, fruits or flowers suffer from discoloration in the pericarp, deterioration of the inside or the shortened shelf life after the fumigation. Thus these chemical injuries, which lower the commercial value of the crops, become a serious problem. However, it is a matter calling for prior settlement to terminate disease and insect pest and thus there is no method of preventing these chemical injuries at present.

PROBLEMS TO BE SOLVED BY THE INVENTION

Under these circumstances, the present invention aims at providing a process for preventing the chemical injuries to vegetables, fruits or flowers caused by methyl bromide and an agent for eliminating methyl bromide.

MEANS FOR SOLVING THE PROBLEMS

It has been reported that the chemical injuries caused by methyl bromide cannot be prevented simply by eliminating the methyl bromide in the atmosphere in which vegetables, fruits or flowers are placed and that it is important to quickly eliminate the methyl bromide existing on the surface of the vegetables, fruits or flowers and, further, invading the inside thereof. Accordingly, the present inventors have conducted extensive studies on agents for quickly eliminating methyl bromide existing on the surface of vegetables, fruits or flowers and invading the inside thereof. As a result, they have found out that the chemical injuries caused by methyl bromide can be prevented and, furthermore, the qualities of the vegetables, fruits or flowers can be effectively maintained after the fumigation by keeping the vegetables, fruits or flowers, which have been fumigated with methyl bromide, together with (A) at least one compound selected from the group consisting of chloric acid, chlorous acid, hypochlorous acid, phosphoric acid, phosphorous acid, hypophosphorous acid and salts thereof and/or (B) an amine, thus completing the present invention.

Accordingly, the present invention relates to:

(1) a process for preventing chemical injuries to vegetables, fruits or flowers caused by methyl bromide by keeping the vegetables, fruits or flowers, which have been fumigated with methyl bromide, together with an agent for eliminating methyl bromide comprising at least one compound selected from the group consisting of chloric acid, chlorous acid, hypochlorous acid, phosphoric acid, phosphorous acid, hypophosphorous acid and salts thereof (hereinafter referred to as the "chemical A") and/or an amine (hereinafter referred to as the "chemical B"); and (2) an agent for eliminating methyl bromide (chemical A) which comprises at least one compound selected from the group consisting of chloric acid, chlorous acid, hypochlorous acid, phosphoric acid, phosphorous acid, hypophosphorous acid and salts thereof.

Now the present invention will be described in detail.

First, the chemical A (the agent for eliminating methyl bromide) will be described.

The chloric acid, chlorous acid, hypochlorous acid, phosphoric acid, phosphorous acid, hypophosphorous acid or salts. (hereinafter referred to as the "compound C") are not particularly restricted. As the salts, alkali metal salts and alkaline earth metal salts etc. may be included. Preferable examples thereof include chlorates, chlorites and hypochlorites (preferably, alkali metal salts and alkaline earth metal salts, such as sodium, potassium, calcium or barium salt), phosphoric acid, phosphorous acid and hypophosphorous acid. The chemical A may further comprise one or more compounds selected from the group consisting of oxides, peroxides, chlorides, carbonates and sulfates of iron, titanium, zirconium, molybdenum, tungsten, zinc, silver, germanium, magnesium, calcium, strontium and barium (hereinafter referred to as the "compound D"). The compound D can improve the performance of the chemical A to eliminate methyl bromide. The compound D may be used at an arbitrary ratio. It is preferable to use from 0 to 95% by weight, still preferably from 5 to 70% by weight, of the compound D based on the total amount of the compounds C and D. It is furthermore preferable to use the compound C, optionally together with the compound D, in the form of a mixture with a commonly employed porous carrier. Preferable examples of the carrier include silica, alumina, silica-alumina, zeolite, talc, diatomaceous earth, Kanuma-tsuchi (pumice), clayey mineral and active carbon. However the present invention is not restricted thereby and any carrier commonly employed in the art may be used therefor. The carrier may be used at an arbitrary ratio. It is preferable to use from 10 to 90% by weight, still preferably from 30 to 70% by weight, of the carrier based on the total amount of the compounds C and D and the carrier. The raw materials to be used to prepare chemical A in the present invention are not particularly restricted. Thus any material which is available may be selected therefor, so long as each component can be obtained therefrom and the aforesaid composition can be finally achieved thereby. The preparation method is not particularly restricted too. For example, the components may be homogeneously mixed with each other as such and then dried and/or calcined, if required. The chemical A thus obtained may be packed in, for example, an air-permeable bag or container either as such (i.e., in powdery form) or after formulating into grains.

Next, the chemical B will be described. The amine is not particularly restricted. Preferable examples thereof include strongly basic amine such as triethylamine, triethylenediamine, hexamethyleneetramine, ethanolamine, morpholine, piperazine and alkylaminopyridine, e.g. ($C_1$–$C_6$ alkyl)aminopyridine. Either one of these amines or a mixture thereof may be used. Although the amine may be used as such, it is preferable, in practice, to use it in a state adsorbed on a porous carrier. The porous carrier is not particularly restricted. Preferable examples thereof include silica, alumina, silica-alumina, zeolite, talc, diatomaceous earth, Kanuma-tsuchi (pumice), clayey mineral and active carbon. It is particularly preferable to use active carbon. The porous carrier and the amine may be used at an arbitrary ratio. It is preferable to use from 5 to 100% by weight, still preferably from 10 to 40% by weight, of the amine based on the total amount of the porous carrier and the amine. Similar to the chemical A, the chemical B may be packed in an air-permeable bag or container. It is also possible to pack a mixture of chemicals A and B in, for example, one bag.

A process of the present invention can be easily carried out by, for example, placing in proximity to vegetables, fruits or flowers the chemical A and/or the chemical B.

After the completion of the fumigation with methyl bromide, vegetables, fruits or flowers are usually packed in corrugated cardboard or polystyrene foam boxes. In the embodiment of the present invention, the chemical A and/or the chemical B may be kept in these boxes together with the vegetables, fruits or flowers. Thus the methyl bromide, even one absorbed in the inside of the vegetables, fruits or flowers, can be eliminated and the chemical injuries caused by the methyl bromide can be prevented. From the viewpoint of keeping the qualities of the vegetables, fruits or flowers thereafter, it is preferable to use the chemical A or a combination of the chemicals A and B. When the chemicals A and B are to be used together, the weight ratio thereof may preferably range from 1:0.01 to 1:100.

The process of the present invention is applicable to all vegetables, fruits or flowers which are to be fumigated. For example, it may be applied to fruits such as apple, citrus fruits (e.g., mandarin orange, orange, lemon or grapefruit), kiwi fruit, persimmon, pear, plum, grape, cherry, apricot, melon and nuts (e.g., peanut, coconut, cashew nut, chestnut or ginkgo nut), vegetables such as celery, lettuce, eggplant, sweet pepper, kidney bean pod, pumpkin, pea, cabbage, onion, asparagus and tomato, and flowers such as carnation, baby's-breath, rose, orchid and anthurium, though the present invention is not restricted thereby.

The amount of the chemical A and/or the chemical B to be used in the process of the present invention may vary depending on the vegetables, fruits or flowers fumigated with methyl bromide. In general, the chemical(s) may be preferably used at a ratio of from 0.001 to 10% by weight, more preferably 0.1 to 5% by weight, based on the vegetables, fruits or flowers.

The vegetables, fruits or flowers, which have been fumigated with methyl bromide, and the chemical A and/or the chemical B may be kept together preferably at a temperature of from −2° to 30° C., though the present invention is not restricted thereby.

According to the present invention, the chemical injuries to vegetables, fruits or flowers caused by methyl bromide can be easily prevented.

The prolonged storage of vegetables, fruits or flowers together with the agent for eliminating methyl bromide or the amine of the present invention does not exert any undesirable effect on the qualities of the vegetables, fruits or flowers.

EXAMPLES

To further illustrate the present invention, and not by way of limitation, the following Examples will be given.

EXAMPLE 1

Apples (Fuji) were fumigated with 40 g/$m^3$ of methyl bromide at 10° C. for 2 hours and then exposed to the open air for 1 hour. 40 g of a chemical, which had been prepared by homogeneously mixing 15 parts by weight of calcium hypochlorite with 85 parts by weight of active carbon, was introduced into an air-permeable bag made of nonwoven fabric, hermetically sealed in a polystyrene foam box together with 10 kg of the apple treated as described above, and stored at 0° C. for 15 days. Separately, a control experiment was performed in the same manner as the one described above except introducing no chemical into the box. As a result, obvious chemical injuries caused by methyl bromide (i.e., browning of the pericarp and the inside of the sarcocarp) were observed in the control case where no chemical was used, while no browning was observed in the test case where the chemical was used. On the second day after the initiation of the storage, the methyl bromide contained in the atmospheric gas and the inside of the sarcocarp of the apples in each case was analyzed. As a result, a trace amount of methyl bromide was detected from the gas in the box and the inside of the sarcocarp of the apples of the control case. In contrast, no methyl bromide was detected from the gas in the box and the inside of the sarcocarp of the apples of the test case.

EXAMPLES 2 AND 3

A chemical was produced by the same method as the one of the Example 1 except that the calcium hypochlorite used therein was replaced by sodium chlorite (Example 2) or potassium chlorate (Example 3). Then using each chemical thus obtained, a test was carried out in the same manner as in the Example 1. The results thus obtained were almost the same as those obtained in the test case of the Example 1.

EXAMPLE 4

60 parts by weight of a 50% aqueous solution of hypophosphorous acid and 70 parts by weight of active carbon were homogeneously mixed and dried at 110° C. 20 g of the chemical thus obtained was introduced into an air-permeable bag and then hermetically sealed in a corrugated cardboard box together with 300 g of immature kidney bean pods, which had been fumigated with 40 g/$m^3$ of methyl bromide at 20° C. for 3 hours, followed by allowing to stand at 25° C. for 2 days. On the other hand, a control experiment was performed in the same manner as the one described above except introducing no chemical into the box. As a result, the pods turned yellow and withered in the control case where no chemical was used, while no such chemical injury was observed in the test case where the chemical was used.

EXAMPLES 5 AND 6

A chemical was produced by the process of the Example 4 except that the hypophosphorous acid used therein was replaced by a 50% aqueous solution of phosphorous acid (Example 5) or a 50% solution of phosphoric acid (Example 6). Using each chemical thus obtained, a test was carried out in the same manner as in the Example 4. The results thus obtained were almost the same as those obtained in the test case of the Example 4.

EXAMPLE 7

15 parts by weight of calcium hypochlorite, 10 parts by weight of ferric oxide and 75 parts by weight of active carbon were homogeneously mixed in a powdery state. 20 g of the chemical thus obtained was introduced into an air-permeable bag and then hermetically sealed in a corrugated cardboard box together with 5 kg of pears (20-seiki), which had been fumigated with 40 g/m$^3$ of methyl bromide at 20° C. for 3 hours, followed by allowing to stand at 15° C. for 10 days. On the other hand, a control experiment was performed in the same manner as the one described above except introducing no chemical into the box. As a result, the pears suffered from the browning in the inside of the sarcocarp in the control case where no chemical was used, while no such chemical injury was observed in the test case where the chemical was used. On the second day after the initiation of the storage, the methyl bromide contained in the atmospheric gas and the inside of the sarcocarp of each case was analyzed. As a result, a trace amount of methyl bromide was detected from the gas in the box and the inside of the sarcocarp of the pears of the control case. In contrast, no methyl bromide was detected from the gas in the box and the inside of the sarcocarp of the pears of the test case.

EXAMPLE 8

15 parts by weight of calcium hypochlorite, 10 parts by weight of ferric oxide, 10 parts by weight of zinc oxide and 65 parts by weight of active carbon were homogeneously mixed in a powdery state. 40 g of the chemical thus obtained was introduced into an air-permeable bag and then hermetically sealed in a polystyrene foam box together with 10 kg of apples (Fuji), which had been fumigated with methyl bromide in the same manner as the one described in the Example 1, followed by allowing to stand at 0° C., for 15 days and then at 15° C., for additional 15 days. Separately, a control experiment was performed in the same manner as the one described above except introducing no chemical into the box. As a result, the apples suffered from the browning in the pericarp and the inside of the sarcocarp in the control case where no chemical was used, while no such chemical injury was observed but the apples maintained the freshness like that in an beginning stage in the test case where the chemical was used. On the second day after the initiation of the storage, no methyl bromide was detected from the gas in the box and the inside of the sarcocarp of the apples of the test case.

EXAMPLES 9 TO 18

A chemical was produced by the process of the Example 7 except that the ferric oxide used therein was replaced by titanium oxide (Example 9), zirconium oxide (Example 10), molybdenum oxide (Example 11), tungsten trioxide (Example 12), silver oxide (Example 13), germanium oxide (Example 14), magnesium carbonate (Example 15), calcium peroxide (Example 16), strontium oxide (Example 17) or barium sulfate (Example 18). Using each chemical thus obtained, a test was carried out in the same manner as in the Example 7. The results thus obtained were almost the same as those obtained in the test case of the Example 7.

EXAMPLES 19 TO 21

30 parts by weight of sodium hypophosphite (Example 19), sodium phosphite (Example 20) or sodium phosphate (Example 21) was homogeneously mixed with 70 parts by weight of active carbon. By using 20 g of the chemical thus obtained, the procedure of the Example 4 was repeated. The results obtained in each case were almost the same as those obtained in the test case of the Example 4.

EXAMPLE 22

Storage test of apples was carried out in the same manner as the one described in the Example 1, except that the chemical used therein was replaced by 20 g of active carbon impregnated with 20% by weight of triethylenediamine. The results thus obtained were almost the same as those obtained in the test case of the Example 1.

EXAMPLE 23

The procedure of the Example 22 was repeated except that the triethylenediamine used therein was replaced by hexamethylenetetramine. The results thus obtained were almost the same as those obtained in the test case of the Example 1.

EXAMPLE 24

5 kg of kiwi fruits, which had been fumigated with 4 g/m$^3$ of methyl bromide at 20° C., for 3 hours, were introduced into a corrugated cardboard box and hermetically sealed together with 10 g of the chemical obtained in the Example 8 and 10 g of the chemical obtained in the Example 22, which were separately packed in air-permeable bags, followed by allowing to stand at 15° C., for 15 days. Separately, a control experiment was performed in the same manner as the one described above except introducing no chemical into the box. As a result, the kiwi fruits of the control case where no chemical was used were softened and suffered from soft rot, while those of the test case where the chemicals were used never showed such chemical injuries.

EXAMPLES 25 TO 26

5 kg of Japanese persimmons (Fuyu) which had been fumigated with 48 g/m$^3$ of methyl bromide at 15° C., for 2 hours (Example 25) or 5 kg of mandarin oranges (Unshu) which had been fumigated with 48 g/m$^3$ of methyl bromide at 15° C., for 2 hours (Example 26) were introduced into a corrugated cardboard box and hermetically sealed together with 10 g of the chemical obtained in the Example 8 and 10 g of the chemical obtained in the Example 22, which were separately packed in air-permeable bags, followed by allowing to stand at 5° C., for 15 days. As a result, Japanese persimmons and mandarin oranges did not show any chemical injuries.

EXAMPLES 27 TO 50

The procedures of the Examples 1 to 24 were repeated except that each vegetable or fruit employed therein was replaced by 30 baby's-breath flowers. The storage was effected at 15° C., for 3 days. As a result, the flowers of the control case where no chemical was used suffered from chemical injuries, for example, withering and browning, while those of the test case where the chemical was used never showed such phenomena.

EFFECTS OF THE INVENTION

The fumigation with methyl bromide, which is unavoidable in the quarantine of imported or exported vegetables, fruits or flowers, presents a problem of the chemical injuries caused by the residual methyl bromide. According to the present invention, which aims at providing an agent and a process for preventing the aforesaid chemical injuries, the chemical injuries caused by methyl bromide can be prevented over a wide range of vegetables, fruits and flowers.

What is claimed is:

1. A process for preventing chemical injuries to vegetables, fruits or flowers caused by methyl bromide, which comprises keeping the vegetables, fruits or flowers, which have been fumigated with methyl bromide, together with an agent for eliminating methyl bromide comprising (i) at least one compound selected from the group consisting of chloric acid, chlorous acid, hypochlorous acid, phosphoric acid, phosphorous acid, hypophosphorous acid and salts thereof and/or (ii) a strongly basic amine selected from the group consisting of triethylamine, triethylenediamine, hexamethylenetetramine, ethanolamine, morpholine, piperazine and alkylaminopyridine.

2. A process as claimed in claim 1, wherein said agent for eliminating method bromide comprises an alkaline earth metal hypochlorite.

3. A process as claimed in claims 1 or 2, wherein said agent for eliminating method bromide further comprises one or more compounds selected from the group consisting of oxides, peroxides, chlorides, carbonates and sulfates of iron, titanium, zirconium, molybdenum, tungsten, zinc, silver, germanium, magnesium, calcium, strontium and barium.

4. A process as claimed in claim 1, wherein said agent for eliminating method bromide comprises a strongly basic amine selected from the group consisting of triethylamine, triethylenediamine, hexamethylenetetramine, ethanolamine, morpholine, piperazine and alkylaminopyridine.

5. A process as claimed in claim 4, wherein said amine is used in a state adsorbed on a porous carrier.

6. A process as claimed in claim 5, wherein said porous carrier is active carbon.

7. A process as claimed in claims 1, 4, 5 or 6, wherein the at least one compound selected from the group consisting of chloric acid, chlorous acid, hypochlorous acid, phosphoric acid, phosphorous acid, hypophosphorous acid and salts thereof is used together with the amine.

* * * * *